(12) United States Patent
Vogtmeier et al.

(10) Patent No.: US 8,491,188 B2
(45) Date of Patent: Jul. 23, 2013

(54) HIGH-RESOLUTION QUASI-STATIC SETUP FOR X-RAY IMAGING WITH DISTRIBUTED SOURCES

(75) Inventors: Gereon Vogtmeier, Aachen (DE); Joerg Bredno, San Francisco, CA (US); Juergen Weese, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 243 days.

(21) Appl. No.: 12/918,092

(22) PCT Filed: Feb. 19, 2009

(86) PCT No.: PCT/IB2009/050690
§ 371 (c)(1), (2), (4) Date: Aug. 18, 2010

(87) PCT Pub. No.: WO2009/104156
PCT Pub. Date: Aug. 27, 2009

(65) Prior Publication Data
US 2011/0002441 A1   Jan. 6, 2011

(30) Foreign Application Priority Data
Feb. 22, 2008  (EP) .................................... 08101905

(51) Int. Cl.
*H05G 1/02*  (2006.01)
(52) U.S. Cl.
USPC .................................. 378/197; 378/9; 378/21
(58) Field of Classification Search
USPC ................. 378/21, 22, 9, 196, 197, 198
See application file for complete search history.

(56) References Cited

U.S. PATENT DOCUMENTS

| | | | | |
|---|---|---|---|---|
| 3,082,321 | A * | 3/1963 | Le Go | 378/22 |
| 4,057,725 | A * | 11/1977 | Wagner | 378/9 |
| 4,289,969 | A * | 9/1981 | Cooperstein et al. | 378/9 |
| 2001/0048731 | A1* | 12/2001 | Nakamura et al. | 378/4 |
| 2004/0120449 | A1 | 6/2004 | Edic et al. | |
| 2004/0213378 | A1 | 10/2004 | Zhou et al. | |
| 2004/0264628 | A1* | 12/2004 | Besson | 378/5 |
| 2005/0190878 | A1* | 9/2005 | De Man et al. | 378/9 |
| 2005/0226364 | A1 | 10/2005 | Edic et al. | |
| 2007/0009081 | A1 | 1/2007 | Zhou et al. | |
| 2007/0009088 | A1 | 1/2007 | Edic et al. | |
| 2007/0116171 | A1* | 5/2007 | Hsieh et al. | 378/8 |
| 2007/0230654 | A1* | 10/2007 | Chappo et al. | 378/15 |
| 2008/0075344 | A1* | 3/2008 | Nambu et al. | 382/131 |

OTHER PUBLICATIONS

Li et al., "Optimizing 4D cone-beam CT acquisition protocol for external beam radiotherapy", International Journal of Radiation Oncology*Biology*Physics, vol. 67, Issue 4, (Mar. 15, 2007), pp. 1211-1219.*

* cited by examiner

*Primary Examiner* — Glen Kao

(57) ABSTRACT

A method for acquiring X-ray image data of an imaging volume is disclosed, the method using a detector and a distributed X-ray source structure having a plurality of single source elements, which are uniformly distributed with a common pitch to each other, the method comprises moving the distributed X-ray source structure and/or the detector with respect to the imaging volume, importantly, the maximum moving distance $d_{max}$ of the distributed X-ray source structure during the acquisition of the X-ray image data is limited to the length $l_p$ of the pitch. Emitting of X-rays from the distributed X-ray source structure and generating a plurality of signals in response to the X-rays incident upon the detector are executed during the movement.

22 Claims, 3 Drawing Sheets

HIGH-RESOLUTION QUASI-STATIC SETUP FOR X-RAY IMAGING WITH DISTRIBUTED SOURCES

FIELD OF THE INVENTION

The present invention relates to the field of medical imaging, more generally to the field of non-invasive imaging. In particular, the present invention relates to a method of acquiring X-ray image data of an imaging volume and an X-ray imaging system with a distributed X-ray source structure having a plurality of single source elements.

TECHNICAL BACKGROUND

In the following description of the background of the present subject matter reference is made to certain structures and methods. Such references should not necessarily be construed as an admission that these structures and methods qualify as prior art under the applicable statutory provisions. Applicants reserve the right to demonstrate that any of the referenced subject matters do not constitute prior art with regard to the present subject matter.

X-ray imaging systems are utilized for various applications in both medical and non-medical fields. The development of distributed X-ray source structures with a plurality of single sources (e.g. Carbon Nano Tube Emitters=CNT) allows new geometries of X-ray imaging systems. Tomographic imaging systems with distributed sources enable a scanning of the object without moving the X-ray source structure and/or detector just by switching sequentially the single X-ray source structures (no moving elements).

The limitation of the spatial resolution of the X-ray images is linked to the sub-sampling and data acquisition of the projections that is limited by the number and position of single source elements.

Precisely, the pitch of a distributed X-ray source structure limits the number of possible projections in a static geometry. Depending on the number, complexity and size of the single source elements of the source structure only limited spatial resolution can be achieved.

US 2007/0009088 discloses a system and method for imaging using distributed X-ray sources. The system includes a distributed X-ray source and a detector. The distributed X-ray source is configured to emit X-rays from a plurality of emission points arranged in a linear, arcuate or curvilinear segment or a non-planar surface. The detector is configured to generate a plurality of signals in response to X-rays incident upon the detector. During the acquisition period, time is required to move the tube and allow the gantry to become stable during which the object remains unmoved. A stationary, distributed X-ray source would allow rapid switching of source positions, improved image quality since motion is eliminated.

US 2007/0009081 A1 discloses a computed tomography device. The device comprises a distributed X-ray source. The X-ray source comprises a cathode with a plurality of individually programmable electron emitting units that each emit an electron beam upon an application of an electric field, an anode target that emits an X-ray beam upon impact by the emitted electron beam, and a collimator, and an X-ray detecting unit.

It is an object of the present invention to highten spatial resolution of X-ray images and to enable better sub-sampling of an imaging volume using an X-ray imaging system with a distributed X-ray source structure. Further it is an object of the present invention to reduce the acquisition time for patient comfort and health.

SUMMARY OF THE INVENTION

This object may be met by the subject-matter according to one of the independent claims. Advantageous embodiments of the present invention are described in the dependent claims.

According to a first aspect of the invention, a method for acquiring X-ray image data of an imaging volume is proposed. The method uses a detector and a distributed X-ray source structure having a plurality of single source elements, wherein the single source elements are uniformly distributed with a common pitch to each other. The method comprises the steps of moving the distributed X-ray source structure and/or the detector with respect to the imaging volume, wherein the maximum moving distance $d_{max}$ of the distributed X-ray source structure during the acquisition of the X-ray image data is limited to the length $l_p$ of the pitch, emitting X-rays from the distributed X-ray source structure and generating a plurality of signals in response to the X-rays incident upon the detector.

The plurality of single source elements of the distributed X-ray source structure may be arranged lineary on an axis in a plane (1-dimension), or over an area of a plane (2-dimensional array). Both, the lineary arrangement or the 2-dimensional arrangement over the area may be arcuated with at least one predefined radius by the shape of a supporting structure.

The pitch is herewith defined as the distance or angle between the midpoints of adjacent single source elements.

Usually, the said pitch is equal for all elements in at least one direction. In this case the pitch is called common pitch. But as the distributed x-ray source structure can be a linear, an arched, and/or an area X-ray source structure, it shall be understood that the distributed X-ray source have may be more than one common pitch in case of a 2-dimensional array in an exemplary embodiment. Precisel if the array is construed as an N×M matrix, with N single source elements in a first direction (X-direction), and M single source elements in a second direction (Y-direction) it is possible that the common pitch with length $l_{pN}$ in the first direction differs from the common pitch with length $l_{pM}$ of the first direction: $l_{pN} \neq l_{pM}$.

Thus, the movement of the distributed X-ray source structure, may have different maximum moving distances $d_{max}$ of the distributed X-ray source structure in each moving direction during the acquisition of the X-ray image data. The limitation depends for different pitches on the length $l_{pN}$ or $l_{pM}$ in X or Y moving direction.

In other words, after emitting electrons at a first emitting position the movement of the distributed X-ray source structure stops at the latest if midpoints (focal spots) of the single source elements arrives at the first emitting position of midpoints of adjacent single source elements.

The movement of the distributed X-ray source structure is not limited to one or two directions in one aspect of the invention. Rather, movement is possible in all spatial directions. In one embodiment it is preferred, if the movement direction follows the direction of a tangent vector at a defined location fitting the shape of the distributed X-ray source structure.

In one aspect, the X-ray imaging system comprises a detector and a distributed X-ray source structure having a plurality of single source elements. The single source elements are uniformly distributed with a common pitch to each other, the X-ray imaging system method is configured for acquiring X-ray image data of an imaging volume. The distributed X-ray source structure and/or the detector is configured to move with respect to the imaging volume, wherein the maximum moving distance $d_{max}$ of the distributed X-ray source structure during the acquisition of the X-ray image data is limited to the length $l_p$ of the pitch. Further, the distributed X-ray source structure is configured to emit X-rays during a movement of the distributed X-ray source structure and/or the detector. The detector is configured to generate a plurality of signals in response to X-rays incident upon the detector during a movement of the distributed X-ray source structure and/or the detector.

According to one embodiment of the invention, the maximum moving distance $d_{max}$ of the distributed X-ray source structure during the acquisition of the X-ray image data is further limited to the length $l_p$ of the pitch minus a predefined sampling distance $d_{samp}$ according to $d_{max.}=l_p-d_{samp}$.

Further limitations are still possible as e.g. the maximum moving distance $d_{max}$ of the distributed X-ray source structure during the acquisition of the X-ray image data is further limited to ½, ⅓ or ¼ of the length $l_p$ of the pitch. Generally, maximum moving distance $d_{max}=1/n*l_p$, with $n \geq 1$ are in the scope of the invention.

According to another aspect, a slow movement (e.g. sinusoidal) of a few centimeter or even only millimeter of the distributed source structure in addition to a fast repetitive switching scheme allows a great increase in the spatial resolution and image quality since many more additional projections become available. In contrast to full rotation (like CT) or 45°-90° movement of tomosynthesis systems, the movement of such a system would be minimal. This enables better and more patient comfortable designs and at the same time decreased requirements for fast mechanical movements which reduces the costs and complexity of the mechanical system. The velocity of the movement is preferably in-between the range from $0.1 \times 10^{-4}$ m/s to $5 \times 10^{-2}$ m/s.

In one aspect, the movement distance of the source structure during acquisition is maximum the length of the common pitch of the distributed X-ray source structure and therefore, has to be only few centimeters or even millimeters. The pitch is preferably selected from a range between 1 mm and 40 cm. A common pitch selected from a range of 0.1 mm to 10 cm is possible by using e.g. nano tube emitters as single source elements.

According to another aspect, the movement velocity and/or moving distance during one detector frame integration period is limited to the tolerable spatial resolution requirement (movement artifact).

In still another aspect, the movement itself could be a continuous forth and back movement. It is not necessary to have a continuous rotation (like in CT) or a rotation along a part of the circular arc as "standard" tomosynthesis systems do. The complete mechanical setup is easy to implement and the advantage of the fast switching of the sources can be combined with a simple small distance movement to achieve very high resolution sampling.

In another aspect, the movement of the source structure is equivalent to a sinusoidal movement. Said movement could be archived by using means for transforming rotation into linear movements, e.g. by using con rod and crank devices. Said rotation is preferably continuous.

Yet to another aspect of the invention, the actual position of the source structure, the imaging volume of an object to be examined and/or the detector is measured by measuring means. Preferably, a relative position of said objects to each other is measured by measuring means. Preferably, in one aspect the method comprises measuring the actual position of the distributed X-ray source structure and/or the detector and/or an object to be examined during the movement of the distributed X-ray source structure and/or the detector.

In yet another aspect, the movement is overlayed with repeated synchronized sequential switching of the single elements of the X-ray source structure for emitting, preferably along a scan trajectory. Thus, emitting of X-rays takes place during the movement of the distributed X-ray source structure and/or the detector. A motion actuator is used according to a further aspect. The requirement for such motion actuator is low with respect to velocity but a good position accuracy for the definition of the source position is necessary.

According to yet another aspect, the detector generating of a plurality of signals takes place during the movement of the distributed X-ray source structure and/or the detector.

In one aspect of the invention, the position of the source is measured or calculated from the overlay of the position of the selected switched source element and the movement of the source array.

According to a further aspect, the movement speed and the switching speed are linked in a way that for a complete acquisition a continuous trajectory with equidistant sampling points is achieved.

According to yet another aspect, the movement speed and the switching speed are linked in a way that for an acquisition of a predefined level of completeness a trajectory with preferably equidistant sampling points is achieved.

According to yet another aspect the subject matter of the invention is preferably used for CT, μCT, tomosynthesis and other high resolution tomographic imaging applications.

In yet another embodiment the method further comprises detecting a position and/or size of an object of special interest by processing means. The detection can be achieved by automatic interpreting a previously obtained data set of the imaging volume. For example, a part of a patient body, the torso for instance, is examined by the X-ray system in a first examination procedure. This first examination procedure may be statically with regard to the X-ray source structure. In this first examination procedure the emitting X-ray elements are switched for emitting separately, or in predefined groups or all at once. Preferably, to reduce emitting energy, a grid of emitting elements is selected from the plurality of single source elements which has a common grid point distance $d_g$ larger than the common pitch of the distributed X-ray source structure; the common grid point distance may be $d_g=N*l_p$ with $N \geq 2$. No moving is necessary during the first examination procedure. A data set obtained from the detector signals of the said first examination procedure is examined to locate an object of special interest. This examination could be executed automatically with one of the methods well-known in the art, or manually by the operator. The object of special interest may be an organ, e.g. the lung, the heart, or parts of an organ.

According to a further aspect of the embodiment of the method, a group of single source elements from the plurality of single source elements are selected in a next step wherein the selection depends on the size and/or the position of the object of special interest. Preferably all single source elements are selected, whose emitting beam/focus overlays at least partially the volume of the organ of special interest.

It shall be understood that the selecting may be executed for more than one organ.

According to another aspect, the selection of single sources could be done manually by an operator.

According to another aspect, the selection of single sources could be done automatically by using a image model with typical object sizes and positions. In this alternative method step the operator may define one object of special interest. Depending from the size of the objects size and position in the model image, which may be artificial or a medical image, the single source elements whose emitting focus crosses the model images relevant area of the selected organ are selected for later (second) examination according to claim 1 of the method.

Other selection criteria may be applied in one other embodiment of the invention, wherein the selection criteria comprises image quality, total dose of emitted radiation, user decision, quantitative acquisition threshold, ration of resolution, acquisition time.

In a second examination procedure, the method according to claim 1 is executed.

Precisely, only the previously selected single source elements and/or the single elements of the detector are switched for emitting in a predefinable progression during the movement of the X-ray source structure.

Thus, the radiation exposure is significantly reduced, nevertheless the examination of the relevant part of the imaging volume, the object of special interest, is examined with high special resolution in a most accurate manner.

It has to be noted that embodiments of the invention are described with reference to different subject matters. In particular, some embodiments are described with reference to the method, whereas other embodiments are described with reference to the X-ray source structure. However, a person skilled in the art will gather from the above and the following description that, unless other notified, in addition to any combination of features belonging to one type of subject matter also any combination between features relating to different subject matters is considered to be disclosed with this application.

The aspects defined above and further aspects, features and advantages of the present invention can be derived from the examples of embodiments to be described hereinafter and are explained with reference to the examples of embodiments. The invention will be described in more detail hereinafter with reference to examples of embodiments but to which the invention is not limited.

Figure 1:
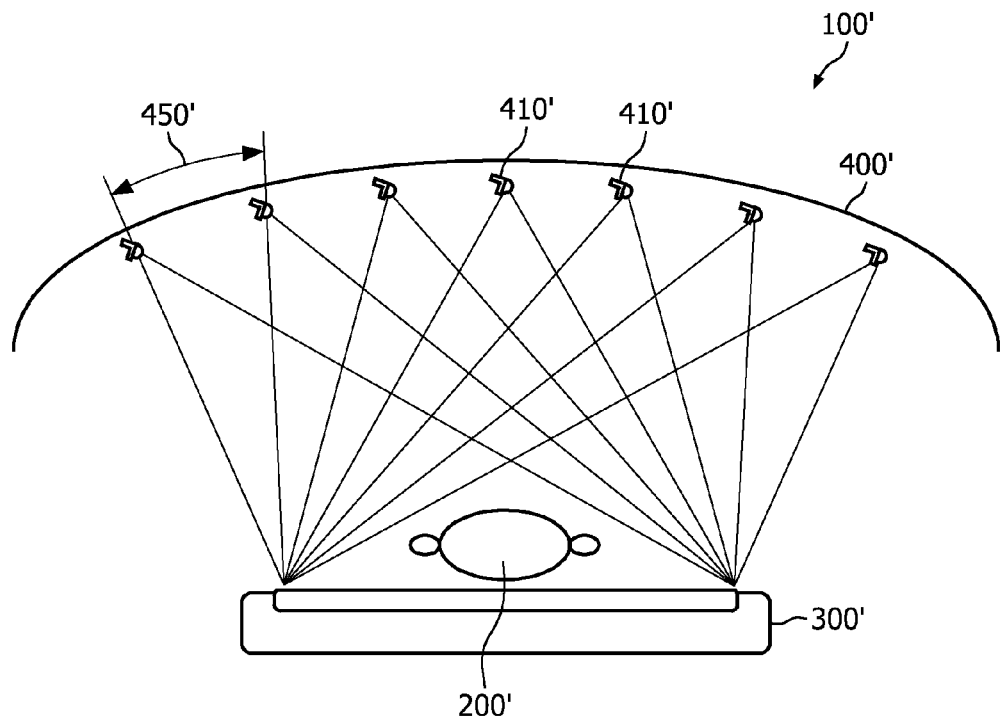
FIG. 1 shows a static tomosynthesis system with a distributed X-ray source structure.

The illustration in the drawings is schematically only.

DETAILED DESCRIPTION OF PREFERRED EMBODIMENTS

A tomosynthesis system 100' for executing a method for acquiring X-ray image data of an imaging volume of a patients body 200' is shown in FIG. 1. The system comprises a detector 300' and a distributed X-ray source structure 400' having a plurality of single source elements 410', wherein the single source elements 410' are uniformly distributed with a common pitch 450' to each other (arrow). The single source elements are Carbon Nano Tubes (CNT). Neither the distributed X-ray source structure 400' nor the detector 300' are able to move in this embodiment.

Figure 2:
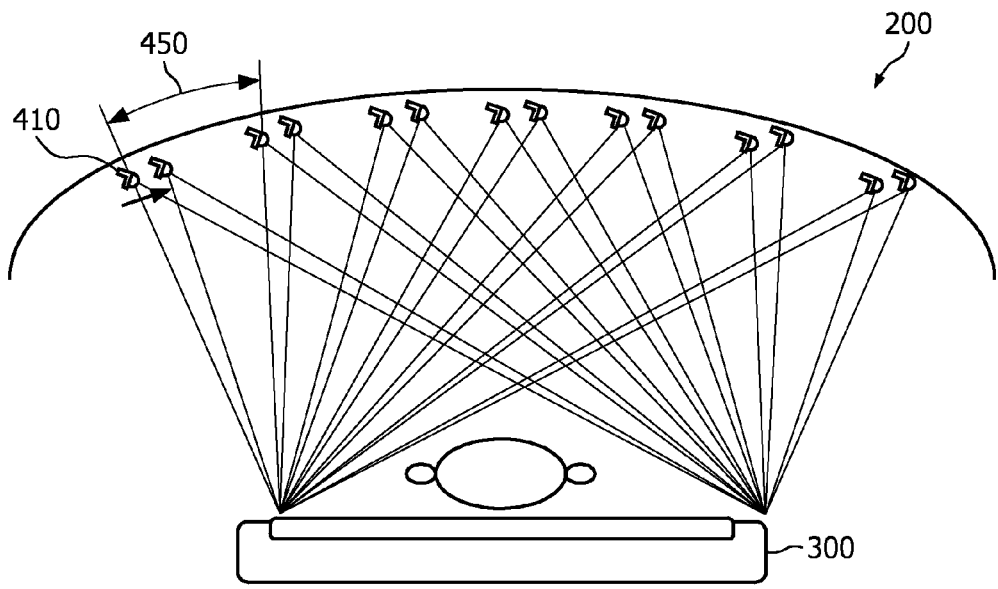
FIG. 2 shows a quasi static tomosynthesis system allowing limited movement along the source bow, wherein the maximum moving distance is equal to the source pitch.

FIG. 2 shows a quasistatic tomosynthesis system 200 for executing a method according to claim 1. The system comprises a detector 300 and a distributed X-ray source structure 400 having a plurality of fixed single source elements 410, wherein the single source elements 410 are uniformly distributed with a common pitch 450 to each other (arrow). The single source elements are Carbon Nano Tubes (CNT). The system 200 enables to move the distributed X-ray source structure 200 with respect to the imaging volume. Alternatively the system 200 enables to move the distributed X-ray source 200 structure and the detector 300 with respect to the imaging volume in another embodiment.

Alternatively the system 200 enables to move the detector 300 with respect to the imaging volume in another embodiment. The maximum moving distance $d_{max}$ of the distributed X-ray source structure during the acquisition of the X-ray image data is in each embodiment according to the invention always limited to the length $l_p$ of the pitch 450. According to FIG. 2, X-rays are emitted with focus 460 from the distributed X-ray source structure. A smaller emitting focus of a few degrees, e.g. limited to 15°, 20° or 30° for each single emitting element is still possible. The distributed X-ray source is configured to emit X-rays from a plurality of emission points, the single source elements, arranged in a linear, arcuate or curvilinear segment or a non-planar or even planar surface. Preferably, the trajectory of the movement of the source structure corresponds to the shape of the source structure. Each of the plurality of single source elements or individually programmable electron emitting units of the x-ray source structure can be operated in a particular sequence or as a group in a particular pattern to produce an emitted x-ray that illuminates the object in the system from a different angle, plane or other orientation. Accordingly, by repeating steps of applying, focusing, impacting, collimating, passing, detecting, and recording with respect to a particular switching sequence or grouping of individually programmable electron emitting units, multiple detected x-ray radiation images can be produced during a movement of the source structure. In one other embodiment the support (patient table) for the examined object is able to move. Thus a multiple helical scanning of the imaging volume is possible.

Figure 3:
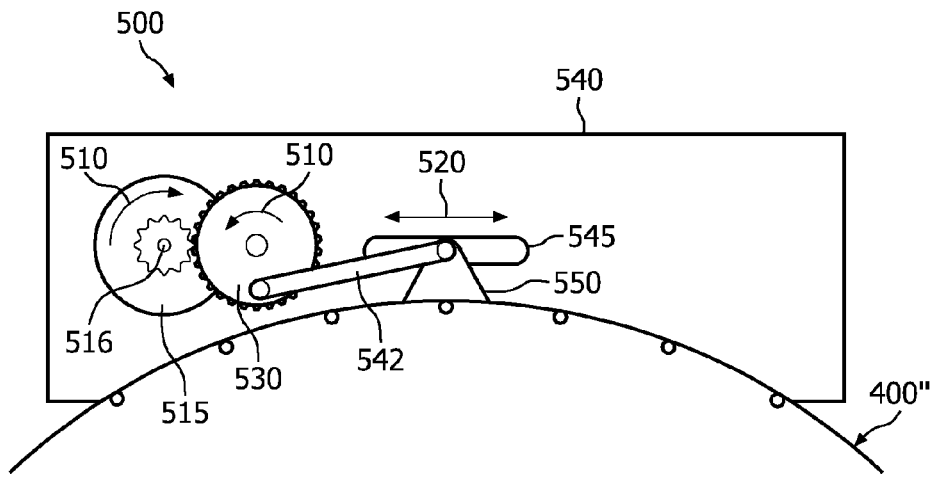
FIG. 3 shows transforming means for transforming a rotating movement to a linear movement of a distributed X-ray source structure.

FIG. 3 shows an embodiment according to one aspect of the invention. Means 500 for transforming rotating movement as indicated by arrow 510 into linear movement as indicated by arrow 520 are realized by using a motor 515 with a gearwheel 516 and transformation means 540. A second gearwheel 530 with a con rod 542 is engaged with the gearwheel 516 of the motor 515. The con rod 542 is guided on one end in a slotted link 545. The distributed X-ray source structure 400" is fixed with fixation means 550 to the con rod 542. Thus the X-ray source structure 400" is able to move in a continuously forth and back movement (520). With the said embodiment the movement velocity of the X-ray source structure 400" changes in sinusoidal manner.

X-ray imaging system further comprises means for transforming rotation in a linear movement for the distributed X-ray source structure.

Figure 4:
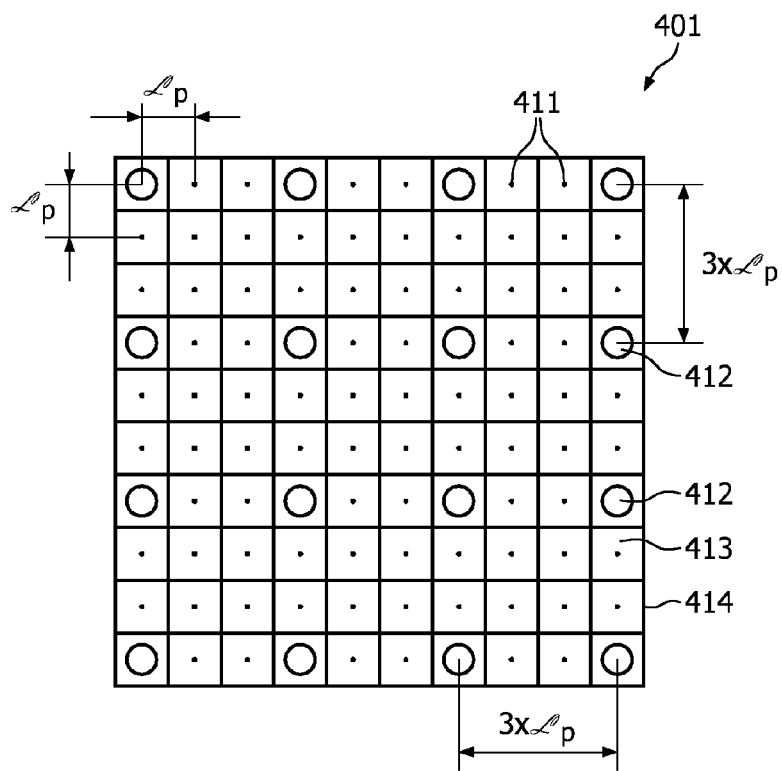
FIG. 4 shows a distributed X-ray source structure.

FIG. 4 shows a distributed X-ray source structure in form of an embodiment 401. The embodiment may comprise a field emission cathode structure comprising a nanostructure or nanotube film (dots 411 and circles 412) on a conducting substrate preferably with a desired metal interlayer 413, wherein the film is patterned and aligned with the openings in a gate electrode 414 to minimize overheating of the metal grid caused by bombardment with the field emitted electrons. The film forms the single source elements 411, 412. Non-active single source elements are shown as dots 411, emitting single source elements are shown as circles 412. All elements 411, 412 have a common pitch with a length $l_p$. The distance between emitting elements 412 is exemplary shown with $3*l_p$.

Figure 5:
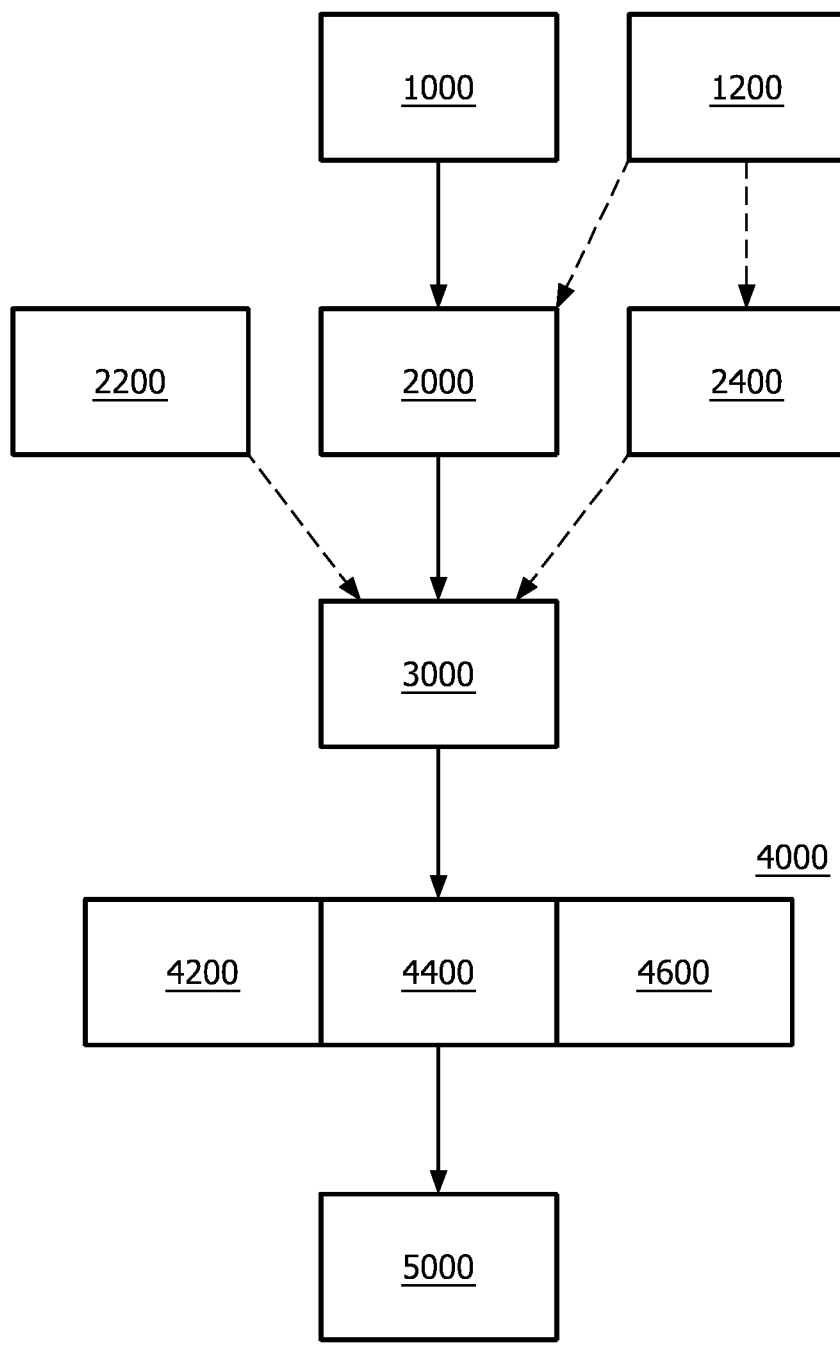
FIG. 5 shows a flow chart according to different embodiments a method for acquiring X-ray image data of an imaging volume.

According to the flow chart of FIG. 5 one exemplary method for acquiring image data comprises detecting a position and/or size of an object of special interest by processing means. The detection can be achieved by automatic interpreting a previously obtained data set of the imaging volume. For example, a part of a patient body, the torso for instance, is examined by the X-ray system in a first examination procedure 1000. In this first examination procedure the emitting X-ray elements are switched for emitting separately, or in predefined groups or all at once. Preferably, to reduce emitting energy, a grid of emitting elements is selected from the plurality of single source elements which has a common grid point distance $d_g$ larger than the common pitch of the distributed X-ray source structure; the common grid point distance may be $d_g=N*l_p$ with $N\geq 2$. FIG. 4 shows such a grid of emitting single source elements as circles 412. No moving is necessary during the first examination procedure. A data set obtained from the detector signals of the said first examination procedure is examined in the next step 2000 to locate an object of special interest. This examination could be executed automatically with one of the methods well known in the art (scout imaging), or manually by the operator. The object of special interest may be an organ, e.g. the lung, the heart, or parts of an organ.

According to a further aspect of the embodiment of the method, a group of single source elements from the plurality of single source elements are selected in a next step 3000 wherein the selection depends on the size and/or the position of the object of special interest. Preferably all single source elements are selected, whose emitting beam/focus overlays at least partially the volume of the organ of special interest.

It shall be understood that the selecting may be executed for more than one organ.

According to an other aspect, the selection of single sources could be done manually by an operator (step 2200).

According to another aspect, the selection of single sources could be done automatically by using a image model with typical object sizes and positions. In this alternative method step 1200 the operator may define one object of special interest. Depending from the size of the objects size and position in the model image (2400), which may be artificial or a medical image, the single source elements whose emitting focus crosses the model images relevant area of the selected organ are selected for later (second) examination according to claim 1 of the method (step 3000, 4000).

In a second examination procedure, the method according to claim 1 is executed in step 4000. The method comprises: moving (4200) the distributed X-ray source structure and/or the detector with respect to the imaging volume, wherein the maximum moving distance $d_{max}$ of the distributed X-ray source structure during the acquisition of the X-ray image data is limited to the length $l_p$ of the pitch; emitting (4400) X-rays from the distributed X-ray source structure, precisely from the selected single source elements, and generating (4600) a plurality of signals in response to the X-rays incident upon the detector. Precisely, only the previously selected single source elements and/or the single elements of the detector are switched for emitting in a predefinable progression during the movement of the X-ray source structure. Finally a final image of the image volume or a part of it is acquired in step 5000. With the said embodiment, radiation exposure is significantly reduced, nevertheless the examination of the relevant part of the imaging volume, the object of special interest, is examined with high special resolution in a most accurate manner.

It should be noted that the term "comprising" does not exclude other elements or steps and the "a" or "an" does not exclude a plurality. Also elements described in association with different embodiments may be combined. It should also be noted that reference signs in the claims should not be construed as limiting the scope of the claims.

The invention claimed is:

1. A method for acquiring X-ray image data of an imaging volume, the method using a detector and a distributed X-ray source structure having a plurality of single source elements, wherein the single source elements are uniformly distributed with a common pitch to each other, the method comprises:
   moving the distributed X-ray source structure and/or the detector, wherein the maximum moving distance $d_{max}$ of the distributed X-ray source structure during the acquisition of the X-ray image data is limited up to the length $l_p$ of the pitch, wherein the movement velocity changes in a saw-tooth-like or sinusoidal manner;
   emitting X-rays from the distributed X-ray source structure; and
   generating a plurality of signals in response to the X-rays incident upon the detector.

2. The method of claim 1, wherein the emitting of X-rays takes place during the movement of the distributed X-ray source structure and/or the detector.

3. The method of claim 1, wherein the generating of a plurality of signals takes place during the movement of the distributed X-ray source structure and/or the detector.

4. The method of claim 1, wherein the method further comprises:
   detecting a position andfor size of an object of special interest by processing means.

5. The method of claim 1, wherein the method further comprises selecting of a group of single source elements from the plurality of single source elements for emitting.

6. The method of claim 5, wherein the selection of the group of single source elements depends on the position and/or the size of an object of special interest of the imaging volume and/or a predetermined data set.

7. The method of claim 1, wherein the maximum moving distance $d_{max}$, of the distributed X-ray source structure during the acquisition of the X-ray image data is further limited to the length $l_p$ of the pitch minus a predefined sampling distance $d_{samp}$ according to $d_{max}=l_p-d_{samp}$.

8. The method of claim 1, wherein the velocity of the movement during one integration period of the detector is limited to a predefined spatial resolution requirement.

9. The method of claim 1, wherein the pitch is selected from the range from 1 mm to 40 cm.

10. The method of claim 1, wherein the sampling distance $d_{samp}$ is predefined between 1 μm to 10 cm.

11. The method of claim 1, further comprising: measuring the actual position of the distributed X-ray source structure and/or the detector during the movement of the distributed X-ray source structure and/or the detector.

12. The method of claim 1, further comprising: sequentially switching of the single source elements for emitting X-rays.

13. The method claim 1, wherein the acquisition of X-ray image data of the image volume is archived by switching single source elements with equidistant sampling, points relative to the imaging volume and moving the distributed X-ray source structure along a predefined trajectory.

14. The method of claim 1, wherein the movement of the distributed X-ray source structure is a continuously forth and back movement.

15. X-ray imaging system comprising a detector and a distributed X-ray source structure having a plurality of single source elements, wherein the single source elements are uniformly distributed with a common pitch to each other, the X-ray imaging system is configured for acquiring X-ray image data of an imaging volume, wherein the distributed X-ray source structure and/or the detector is configured to move; wherein the maximum moving distance $d_{max}$ of the distributed X-ray source structure during the acquisition of the X-ray image data is limited up to the length $l_p$ of the pitch; wherein the distributed X-ray source structure is configured to emit X-rays during a movement of the distributed X-ray source structure and/or the detector; and wherein the detector is configured to generate a plurality of signals in response to X-rays incident upon the detector during a movement of the distributed X-ray source structure and/or the detector, wherein the X-ray imaging system further comprises means for transforming rotation into a linear or non-linear movement of the distributed X-ray source structure; wherein the linear or non-linear movement is mechanically limited up to the length of the common pitch.

16. An X-ray device configured for acquiring X-ray image data of an imaging volume, said device comprising:

a detector; and a distributed X-ray source structure that has a plurality of single source elements, said elements being, in at least one direction, uniformly distributed with a common pitch to each other, said device being further configured with a maximum range of moving said structure forth and back during said acquiring, said maximum range being limited up to a length of said pitch that corresponds to a direction from among said at least one direction, said device configured for emitting X-rays from said structure and for generating a plurality of signals in response to said X-rays that are incident upon said detector.

17. The device of claim 16, configured with a mechanical limitation that defines said maximum range.

18. The device of claim 16, said moving occurring in a movement direction that corresponds, at a point along a periphery of said structure, to a direction of a tangent vector to said point.

19. The device of claim 18, comprising a connecting rod for causing said moving, said rod connected to said point and configured for pivoting into alignment with said movement direction while applying force to said structure.

20. The device of claim 16, configured such that at least one of said moving and moving said detector is with respect to said imaging volume.

21. The device of claim 16, configured such that the moving forth and the moving back are each limited to within said maximum range.

22. The device of claim 16, configured such that a velocity of said moving changes in a saw-tooth-like or sinusoidal manner.

* * * * *